(12) United States Patent
Au et al.

(10) Patent No.: US 12,426,867 B2
(45) Date of Patent: Sep. 30, 2025

(54) SYSTEMS AND METHODS FOR ORGAN RETRACTION AND SPACE OPENING

(71) Applicants: The Chinese University of Hong Kong, Shatin (CN); Retraction Limited, Hong Kong (CN)

(72) Inventors: Kwok Wai Samuel Au, Shatin (CN); Hoi Wut Yip, Shatin (CN); Tsz Yin Chung, Tseung Kwan O (CN); Stuart Moran, Hong Kong (CN)

(73) Assignees: The Chinese University of Hong Kong, Shatin (CN); Microline Surgical, Inc., Beverly, MA (US)

( * ) Notice: Subject to any disclaimer, the term of this patent is extended or adjusted under 35 U.S.C. 154(b) by 563 days.

(21) Appl. No.: 17/602,723

(22) PCT Filed: Apr. 10, 2020

(86) PCT No.: PCT/CN2020/084115
§ 371 (c)(1),
(2) Date: Oct. 8, 2021

(87) PCT Pub. No.: WO2020/207455
PCT Pub. Date: Oct. 15, 2020

(65) Prior Publication Data
US 2022/0167958 A1 Jun. 2, 2022

Related U.S. Application Data

(60) Provisional application No. 62/832,097, filed on Apr. 10, 2019.

(51) Int. Cl.
*A61B 17/02* (2006.01)
*A61B 17/00* (2006.01)
(Continued)

(52) U.S. Cl.
CPC .......... *A61B 17/0218* (2013.01); *A61B 34/32* (2016.02); *A61B 34/71* (2016.02);
(Continued)

(58) Field of Classification Search
CPC ............... A61B 17/0218; A61B 34/76; A61B 2034/2065; A61B 2017/00022; A61B 2017/00867; A61B 2017/0287
See application file for complete search history.

(56) References Cited

U.S. PATENT DOCUMENTS 7,862,498 B2 * 1/2011 Nguyen ............... A61N 5/1015
600/7
9,901,408 B2 * 2/2018 Larkin ............... A61B 1/00193
(Continued)

FOREIGN PATENT DOCUMENTS

CN 101287417 A 10/2008
CN 102695541 A 9/2012
(Continued)

OTHER PUBLICATIONS

International Search Report and Written Opinion for International Application No. PCT/CN2020/084115, mailed Jun. 30, 2020, 14 pages.

*Primary Examiner* — Eduardo C Robert
*Assistant Examiner* — Holly Joanna Lane
(74) *Attorney, Agent, or Firm* — Kilpatrick Townsend & Stockton LLP

(57) ABSTRACT

Robotic organ retraction systems, devices (200), and methods. Organ retraction devices (200) may include compliant retractor tips, articulating joints (702), integrated force sensors (408, 410), and automatic retraction capability to enable safe and efficient organ retraction.

19 Claims, 11 Drawing Sheets

(51) Int. Cl.
- *A61B 18/00* (2006.01)
- *A61B 34/00* (2016.01)
- *A61B 34/30* (2016.01)
- *A61B 34/32* (2016.01)
- *A61B 90/00* (2016.01)
- *A61B 18/12* (2006.01)
- *A61B 34/20* (2016.01)

(52) U.S. Cl.
CPC .... *A61B 34/76* (2016.02); *A61B 2017/00022* (2013.01); *A61B 2017/00867* (2013.01); *A61B 2018/00595* (2013.01); *A61B 2018/126* (2013.01); *A61B 2034/2061* (2016.02); *A61B 2034/2065* (2016.02); *A61B 2034/301* (2016.02); *A61B 2034/306* (2016.02); *A61B 2090/061* (2016.02); *A61B 2090/065* (2016.02)

(56) References Cited

U.S. PATENT DOCUMENTS

| | | | |
|---|---|---|---|
| 10,632,613 B1* | 4/2020 | Yeung | F16H 35/06 |
| 11,259,882 B1* | 3/2022 | Walsh | G16H 20/40 |
| 2006/0052670 A1* | 3/2006 | Stearns | A61B 17/0218 600/216 |
| 2006/0074277 A1* | 4/2006 | Yoshida | A61B 17/0218 600/209 |
| 2007/0142694 A1 | 6/2007 | Cutrer et al. | |
| 2011/0245846 A1* | 10/2011 | Ewers | A61B 17/42 606/139 |
| 2018/0280013 A1* | 10/2018 | Ravikumar | A61L 31/06 |
| 2019/0167650 A1* | 6/2019 | Bekker | A61K 31/506 |
| 2020/0046217 A1* | 2/2020 | Butcher | A61B 1/32 |

FOREIGN PATENT DOCUMENTS

| | | |
|---|---|---|
| CN | 105916450 A | 8/2016 |
| JP | 08317928 A | 12/1996 |
| WO | 2012/114569 A1 | 8/2012 |

* cited by examiner

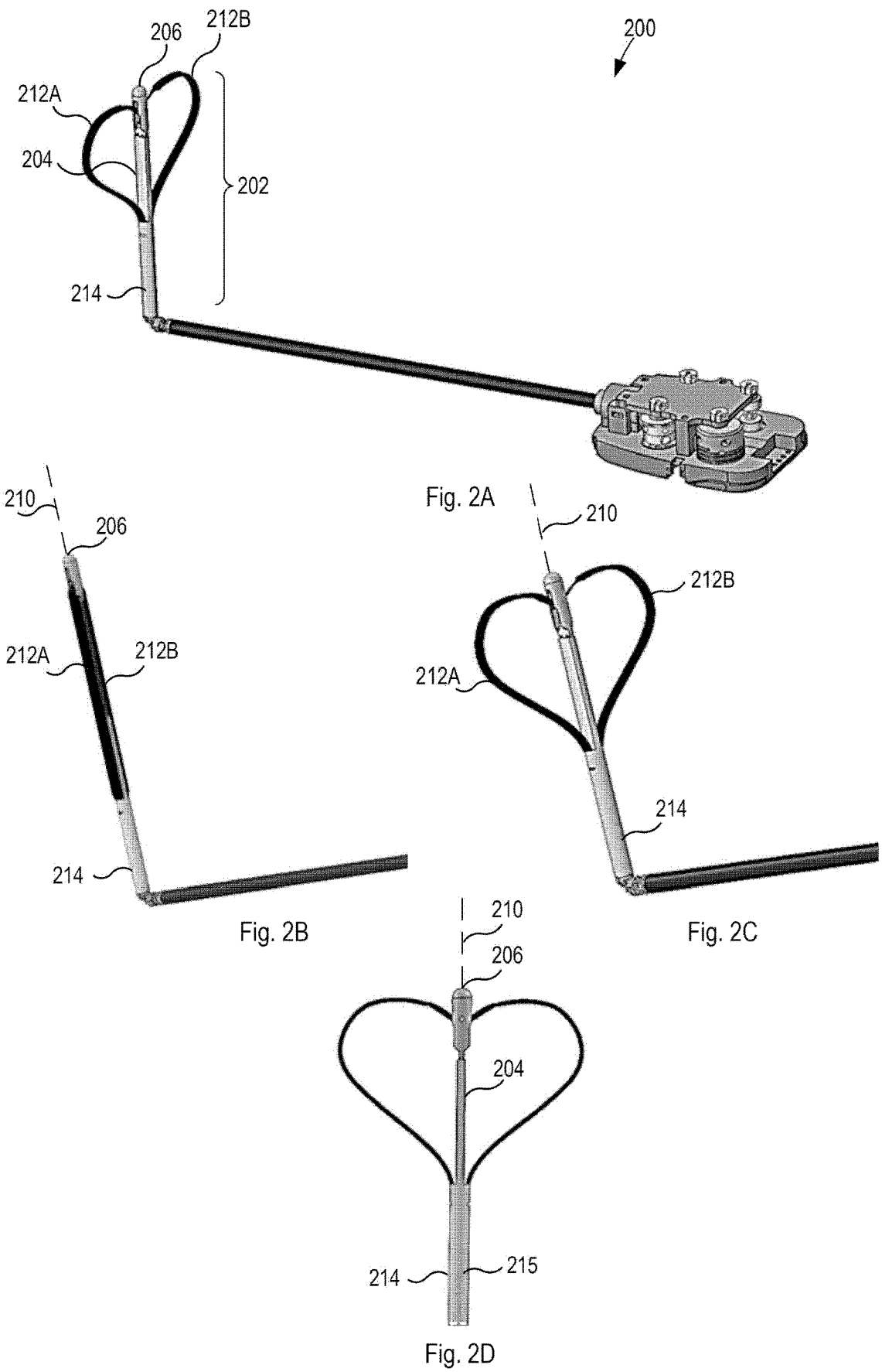

SYSTEMS AND METHODS FOR ORGAN RETRACTION AND SPACE OPENING

FIELD

The present technology relates generally to the field of surgical retractors and space openers.

BACKGROUND

Organ retraction refers to an organ (e.g. muscle, nerve, heart, lung, liver, kidney, intestine, blood vessel, etc) being held aside in order to provide visualisation and/or access to a target surgical site. Space opening similarly refers to expanding spaces in bodily cavities, for example the colon, in order to provide visualisation and/or access to a target surgical site. Organ retraction and space opening are particularly advantageous in minimally invasive surgery wherein space is limited.

Existing retractors and space openers are manually manipulated and comprise rigid structures, for example as shown in FIGS. 1A-C. FIG. 1A shows a grasping Style retractor. FIG. 1B shows a fan-style retractor from Covidien. FIG. 1C shows a robotic retractor for the da Vinci Surgical System. Physicians struggle with controlling and minimizing the force applied onto tissue while positioning existing retractors while maintaining optimal exposure, i.e visualisation and/or access, to a target surgical site.

Accordingly, there exists a need for retractors and space openers that are controllable and able to minimize force applied onto tissue. The present invention fulfills this and other related needs.

SUMMARY

The present technology relates to robotic organ retraction and space opening systems, devices, and methods. As used herein, the term retractor refers to device used for both organ retraction and space opening. The disclosed technology integrates one or more of compliant retractor tips, articulating joints, integrated force sensors, and automatic retraction capability to enable safer and more efficient organ retraction, thereby improving clinical outcomes.

The present technology addresses a problem related to existing retractors which have limited dexterity and offer no feedback on the amount of force that is being applied to tissue, which may lead to unwanted tissue damage. The present technology includes increased dexterity through one or more articulating joints, and further prevents tissues damage with a compliant tip and forcing sensing, both of which allow for control and minimization of force applied to retracted tissue. The applied force and amount of retraction may be fully automated.

The present technology may be used in a variety of surgical applications, including minimally invasive surgeries. The present technology may be used as a retractor and/or a space opener in different clinical applications such as transoral thyroid retraction, liver retraction, colon retraction and a retractor for uterus manipulation.

BRIEF DESCRIPTION OF THE DRAWINGS

The disclosure will be readily understood by the following detailed description in conjunction with the accompanying drawings, wherein like reference numerals designate like structural elements, and in which:

FIGS. 2A-2D show an embodiment of a surgical retractor device of this invention.

DETAILED DESCRIPTION

Figure 1A:
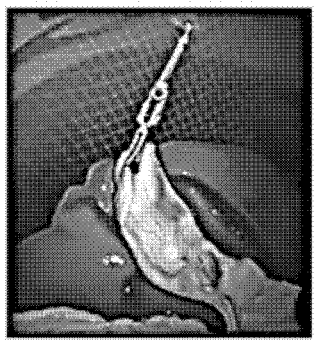
FIGS. 1A-1C show prior art retraction devices.
Figure 1B:
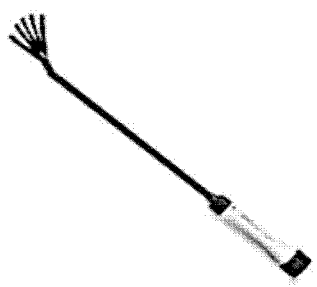
Figure 1C:
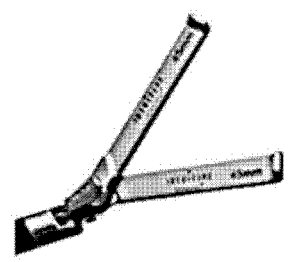

Throughout this description for the purposes of explanation, numerous specific details are set forth in order to provide a thorough understanding of the many aspects and embodiments disclosed herein. It will be apparent, however, to one skilled in the art that the many aspects and embodiments may be practiced without some of these specific details. In other instances, known structures and devices are shown in diagram or schematic form to avoid obscuring the underlying principles of the described aspects and embodiments.

Retractor Device

FIG. 2A shows a surgical retractor device 200. The surgical retractor device 200 may be used for the retraction of a surgical opening and/or an organ in order to provide visualization and/or access to a target surgical site. In embodiments surgical retractor devices comprise a retractor end, an external actuation portion, and one or more shafts connecting the retractor end to the external portion. The retractor end may include a compliant retractor element and may be articulable relative to other portions of the device. For example, as shown in FIG. 2A, surgical retractor device 200 comprises retractor end 202. Retractor end 202 comprises a first shaft 204 comprising a distal end 206 and a proximal end 208, extending along a longitudinal axis 210 of the first shaft 204. In embodiments, the first shaft is straight, however in embodiments the first shaft, and/or other shafts, may include one or more curved portions. Retractor end 202 further comprise a pair of retractor struts 212A and 212B. The retractor struts 212A and 212B extend from the distal end 206 of the first shaft 204 toward the proximal end 208 of the first shaft. The ends of the retractor struts 212A and 212B proximal to the distal end 206 are coupled to the first shaft 204. In embodiments, the coupling may be rotational with a hinge or may be fixedly coupled, for example by adhesive, welding, press fit, screw and/or rivet fastening.

In embodiments, the retractor end 202 further comprises a second shaft 214 extending along the longitudinal axis 210 of the first shaft 204. The ends of the retractor struts 212A and 212B distal to the distal end 206 are coupled to the second shaft 214. The second shaft 214 is translatable relative to the first shaft 204. The first and/or second shaft may be caused to translate relative to the other of the two shafts by an actuator within another shaft of the device and/or may be mechanically coupled to an external actuation portion Translation of the shafts may be cable driven, linkage driven, pneumatically driver, hydraulically, driver, and/or magnetically driver. Translating the second shaft 214 relative to the first shaft 204 so that the distal end 206 is closer to the second shaft 214 causes the retractor struts 212A and 212B to transition from a collapsed configuration, for example as shown in FIG. 2B, to an expanded configuration, for example as shown in FIG. 2C. In embodiments the second shaft 214 comprises a lumen 215 that the first shaft 204 is positioned to translate within, as shown in the cross-section view of FIG. 2D, and in this configuration the first shaft may be referred to as a telescoping push-pull rod. In embodiments, the first shaft comprises a lumen that the second shaft is positioned within so that the first shaft translates outside of the second shaft.

As shown in FIG. 2B, in the collapsed configuration the retractor struts 212A and 212B extend in a substantially straight line parallel to the longitudinal axis 210, and are flush with the first shaft 204. In embodiments, a first shaft may comprise flat side portions for each retractor strut coupled to the first shaft and the retractor struts may have a flat side in order to contact the corresponding flat side portion of the first shaft in order to achieve a compact cross-section in the collapsed configuration with the retractor struts folded against and contacting the first shaft. A compact cross-section in the collapsed configuration is beneficial when navigating the device through a patient's body to a target retraction site. In embodiments, after organ retraction is complete the retractor struts 212A and 212B may be returned to the collapsed configuration from the expanded configuration by translating the second shaft relative to the first shaft in order to navigate the device out of the patient's body in a more compact form in order to prevent collateral tissue damage caused by extraction of the retractor device.

As shown in FIG. 2C, in the expanded configuration the retractor struts 212A and 212B bow away from the longitudinal axis 210 of the first shaft 204. The outer surfaces of the bowed retractor struts form part of a retraction surface for contacting tissues of a patient during organ retraction. The bowing is achieved by the buckling principle of a continuum bending beam mechanism. In the embodiments, the retractor struts 212A and 212B bow in opposite directions from the longitudinal 210 axis in the same plane. Middle portions of retractor struts 212A and 212B extend away from the first shaft 204 for example between 0 mm and 70 mm. In embodiments, the struts may have a maximum bowing displacement for example of 10 mm, 20 mm, 30 mm, 40 mm, 50 mm, 60 mm, or 70 mm. As will be discussed below, in embodiments before or during a surgery the degree of bowing and therefore organ retraction may be continually adjusted to any amount between the minimum and maximum amount using robotic actuators and a feedback system. The degree of bowing of the first pair of retractor struts is based on the length of the retractor struts and the relative position of the second shaft and the distal end of the first shaft. During organ retraction, the degree of bowing has an effect on the amount of force applied against the organ and the amount of retraction of the organ, and is selected and continually adjusted to continually achieve a desired access and visualization of the target surgical site without causing damage to the retracted organ.

In embodiments, for example as shown in FIGS. 2C and 2D, the ends of the retractor struts 212A and 212B proximal to the distal end 206 may be coupled to the first shaft 204 in a direction with a distal component so that the bowed retractor struts 212A and 212B form a heart shape. In embodiments, the ends of the retractor struts 212A and 212B proximal to the distal end 206 may be coupled to the first shaft 204 in a direction perpendicular to the longitudinal axis, or at an angle between perpendicular and toward the proximal end 208.

In an expanded configuration, the shape of the bowed retractor struts when not subject to an outside force, for example a retracted organ contacting the retractor struts, is determined by the material and shape of the components of the retractor struts, as well as the displacement of the second shaft relative to the first shaft. In embodiments, the stiffness/flexibility of the retractor struts is determined by the material selections and cross-sections, and is selected to achieve a compliant retraction surface in order to minimize excessive interaction force and/or stress inadvertently applied to an organ, for example by unexpected patient movement or unintentional movement of the retractor tip toward the retracted organ. In other words, in embodiments it is advantageous for the retractor struts to yield and deform toward the first shaft prior to a damaging force being applied on a tissue. For example, if the retractor tip is contacting a retracted organ and the organ is moved 5 mm closer to the retractor tip, then the bowed retractor strut may deform up to 5 mm toward the first shaft, for example 3 mm, so that the net further retraction of the organ is reduced or cancelled out. In addition to deformation of the retractor struts causing less force on the organ, the deformation may alternatively or additionally cause less stress to be placed on the retracted organ. Specifically, deforming the bowed retractor strut back toward the first shaft causes the portion of the strut contacting the organ to flatten out, thereby increasing the surface area of the strut in contact with the organ which spreads the force over a greater area of the organ which reduces the applied stress to the organ. This is in contrast to existing rigid retractors that include a single static point of contact which results in a high applied stress to an organ since the contact area is not able to change and distribute the force as can be done with the deforming strut of the present technology. In embodiments, the second shaft which the proximal ends of the struts are attached to is configured to release the bowing of the struts when a threshold force, stress, or deflection is detected with a sensor connected to a controller. For example, a force on a strut or the second shaft may be detected, as will be discussed in greater detail below, and the control system will cause the second shaft to translate so that the struts will un-bow rapidly.

Retractor Struts

Figure 4A:
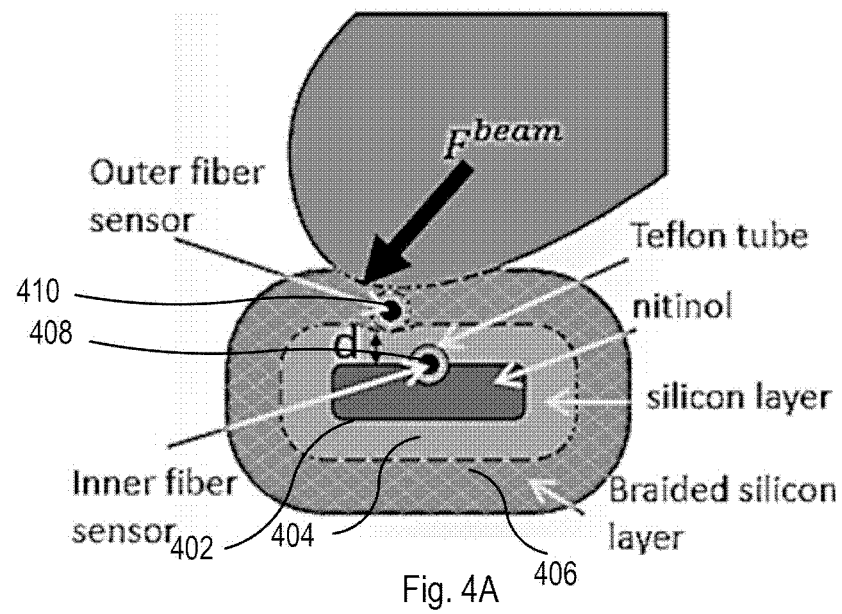
FIGS. 4A and 4B show integrated force sensors in a retractor strut.

In embodiments, the retractor struts comprise multiple layers, for example as shown in FIG. 4A. As shown in the cross-sectional view of FIG. 4A, a retractor strut may comprise a core 402, one or more outer layers 404 and 406, and a one or more sensor elements 408 and 410. In embodiments, the core 402 may comprise a solid beam composed of metal, plastic, and/or a composite. In embodiments, the core 402 is composed of a metal beam for example a spring stainless steel, a composite beam for example carbon fiber, a plastic beam for example polyether ether ketone (PEEK), and/or a shape metal alloy, for example Nitinol. Shape metal alloys are beneficial for transitioning between the straight/flat configuration of the collapsed state, for example as shown in FIG. 2B, and the bowed configuration in the expanded state, for example as shown in FIG. 2C, wherein the translation of the second shaft causes the retractor strut to buckle and due to the elasticity of the beam not permanently deform.

In embodiments, the core may have a rectangular cross-section with the wide sides facing toward and away from the first shaft. This causes the beam to more readily bow so that the wide sides form concave and convex surfaces. In embodiments, the cross-section of the core along the length of the core may be constant or may be variable. The cross-section of the core along the length of the core may be square, circular, elliptical, and/or any other shape. The selection of a constant and/or variable cross-section allows for control of the shape/contours of the retractor struts in the bowed configuration and further allows for selection of the amount of force deliverable, and therefore compliance, by each portion of the retractor strut. For example, the cross-section may be selected for the middle portion of the retractor strut to have more resiliency than the portions coupled to the first and second shafts so that the retractor surface which contacts and organ is most compliant.

In embodiments, the core may be composed of a material configured to have different properties at different temperatures. For example, the core may transition between an austenite state and a martensite state based on the temperature of the core. In embodiments, the core may be composed of a shape metal alloy. A shape metal alloy core may be deformed from an original shape prior to insertion in a patient and then heated in order to return to the original shape. The heating may come from an external source, or a heat source integrated on the retractor device, including integrated within the retractor strut. In embodiments, the original shape is a bowed shape, and prior to insertion the core may be deformed in a flattened shape. The core may be heated when the device is positioned at a target retraction site in order to bow the retractor strut and retract the organ, as discussed above. This type of bowing has the advantage that translation of shafts, as discussed above, does not need to be performed to achieve a transition between the collapsed state and the expanded state. In embodiments, the heating system is controlled by a controller in order to cause the retractor struts to bow.

In embodiments, the core is coated by one or more outer layers. The outer layers may comprise a first outer layer 404. The first outer layer may be a plastic, for example Teflon, polypropylene, nylon, and/or polyethylene terephthalate (PET). The first outer layer may provide protection to the patient from sharp edges of the core. Further, the first outer layer may define the shape of the retractor surface while minimally, if at all, affecting the bowing and compliance of the retractor strut which may be mainly influenced by the core. For example, the first outer layer may be shaped to have rounder surfaces than the core.

The second outer layer 406 may be plastic and be selected to achieve a desired surface characteristic of the retractor strut. For example, the second outer layer may be more resilient than the first outer layer. In embodiments the second outer layer is composed of silicone, polyisoprene, natural rubber, polybutadiene, polyisobutylene, and/or polyurethanes. The second outer layer may have a smooth and/or textured surface portions. For example, the second outer layer may a braided material which has a braided surface that increases friction with the retracted organ during organ retraction compared to a smooth surface. This increased friction prevents the retracted organ from sliding away from the retractor struts.

During organ manipulation and retraction, multiple force contacts between different parts of the retractor occur which may result in different parts of the device deflecting in different ways. Determining the location and amount of force, stress, and deflection of a point on the device, for example a portion of the retractor strut, may be used as direct feedback to a manual operator or feedback in a robotic surgical system to determine positioning parameters for adjusting a surgical device, for example a retractor device. In embodiments, the retractor comprises sensors for detecting deflection and/or force exerted on the retractor struts and/or shafts. The detection results from the sensors may be used to identify contact locations and determine interaction forces at the detected contact points. In embodiments, data from the sensors may be used by a controller and/or user to determine an appropriate amount of force against an organ and/or retraction of an organ by the retractor. In embodiments, the one or more of the retractor struts may comprise one or more force sensors configured to sense external forces on the retractor struts. The force sensor may be electrical, optical, and/or pneumatic. For example, the force sensors may be one or more strain gauges attached along a length of one or more of the retractor struts.

Figure 4B:
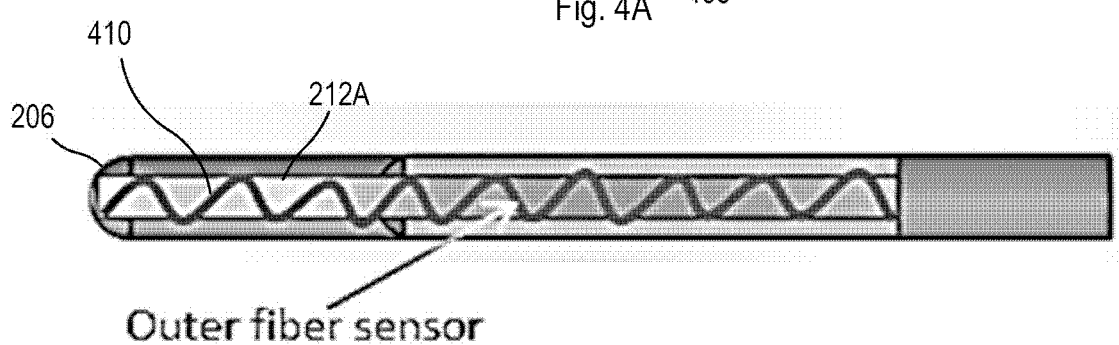
Figure 5A:
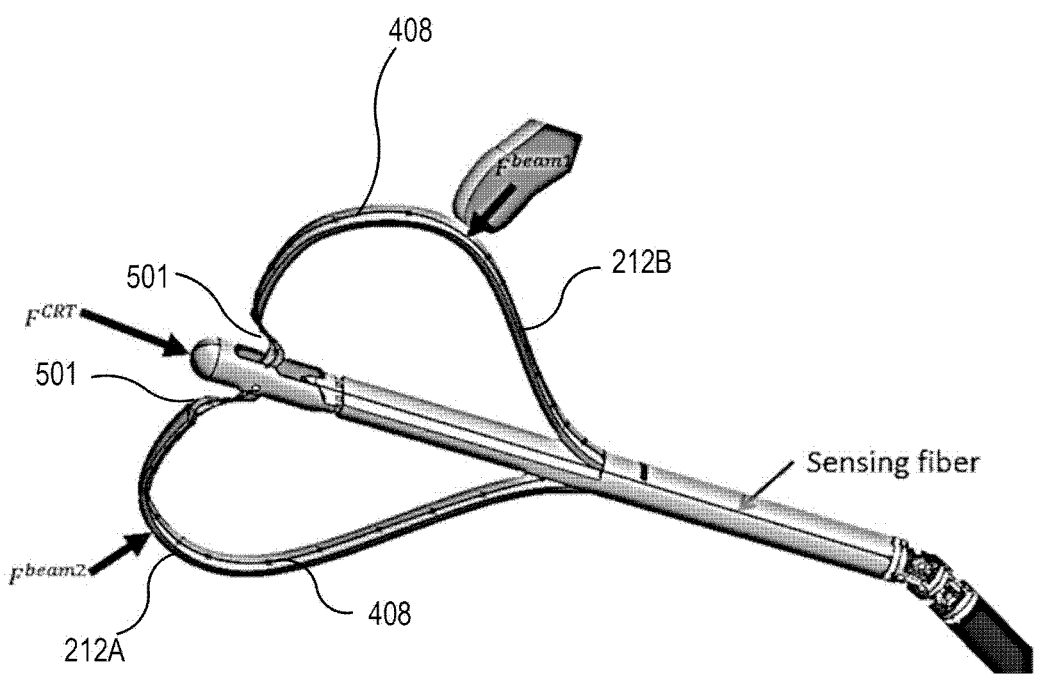
FIGS. 5A and 5B show retractor struts.
Figure 5B:
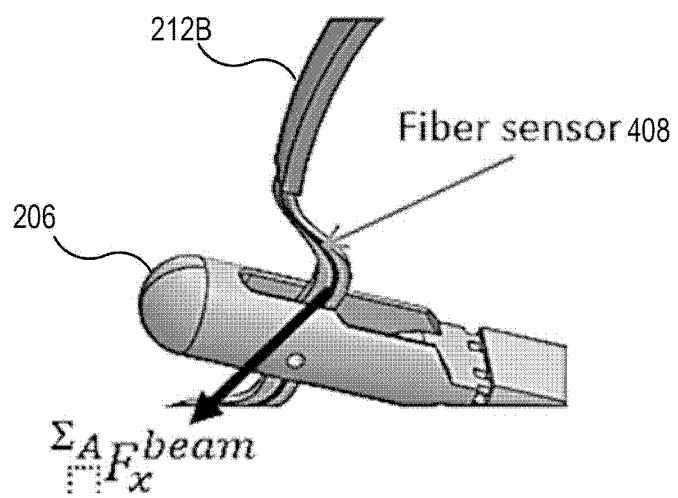

As shown in FIG. 4A, the force sensors may comprise a inner optical fiber sensor 408 extending along the length of the retractor strut between the core 402 and the first outer layer 404. Further, as shown in FIG. 4B, the force sensors may comprise an outer optical fiber sensor 410 extending along the length of the retractor strut between the first outer layer 404 and the second outer layer 406. The optical fibers each comprise at least one fiber Bragg grating sensor that may be used in a robotic surgical system to determine deflection at one or more sections along the length of each refractor strut. The fiber Bragg grating sensors may be used to determine the real time shape of the retractor strut during organ retraction. One or more optical fiber sensors may extend along the length of a retractor strut in a straight line, for example inner fiber sensor 408 as shown in FIG. 4A. Further, one or more optical fibers may extend along the length of the retractor struts in a tortuous path, for example outer fiber sensor 410 as shown in FIGS. 4A and 4B. In embodiments, straight optical fibers may be used to determine deflection measurements and tortuous optical fibers may be used in determining force contact at one or more locations along a retractor strut. Optical fiber sensors provide the advantage of being compact and further not substantially altering the buckling properties of the retractor struts. In embodiments, the end of each retractor strut may include a twist portion 501, as shown in FIGS. 5A and 5B. In embodiments, for example as discussed above and as shown in FIGS. 5A and 5B, a retractor device includes a first shaft, also referred to as a the "rigid" Center Telescoping Rod (CTR, $F^{CTR}$), and two retractor struts, also referred to as buckling beams ($F^{beam1}$, $F^{beam2}$), Each retractor strut may include two FBG-based fibers: (a) an inner fiber sensor locates deep inside the retractor strut and passing through the entire retractor strut in order to provide precise deflection measurement which are used by a controller to estimate the external force; and (b) an outer fiber sensor close to the surface of the retractor strut, passing through a tortuous path. The fiber passing through the tortuous path allows the controller to detect the force contact along the length of the retractor strut. A "Twist" structure, as shown in FIGS. 5A and 5B, is present at each end of the retractor strut. The bending motion of the "Twist" structure is orthogonal to the compression of the bowed retractor strut, allowing for a controller to decouple the "twisting" force component $\Sigma_A F_x^{beam}$ from buckling force component $\Sigma_A F_{y,z}^{beam}$. The twisting force component is used to detect the bending motion orthogonal to the compression of the buckling beams. For example, as taught in [V. Mishra, N. Singh, U. Tiwari, and P. Kapur, "Fiber grating sensors in medicine: Current and emerging applications," Sensors and Actuators A: Physical, vol. 167, no. 2, pp. 279-290, 2011] [S. C. Ryu and P. E. Dupont, "FBG-based shape sensing tubes for continuum robots," Proc IEEE Int. Conf. on Robotics and Automation, Hong Kong, China, pages 3531-3537, June 20114.], both of which are incorporated by reference in their entirety, when a FBG fiber is strained, the change in the Bragg wavelength $\delta\lambda_{Bragg}$ in observed in order to estimate the strain of the fiber as follows:

$$\frac{\delta\lambda_{Bragg}}{\lambda_{Bragg}} = \kappa \in \quad (1)$$

where κ=0.78 is determined by the fiber strain and photo-elastic response. The Bragg wavelength $\delta\lambda_{Bragg}$ can be determined by the Bragg resonance condition: $\lambda_{Bragg}=2n_{eff}\Lambda_{grating}$, where $n_{eff}$ and $\Lambda_{grating}$ are the effective index of the guided mode and the period of the gating respectively. This principle is used to compute the strains of the rigid CTR and the "Twist" section of the buckling beam. FEA simulation may be performed in order to create a realistic parametric model to predict the interaction force acting on these parts.

Figure 13:
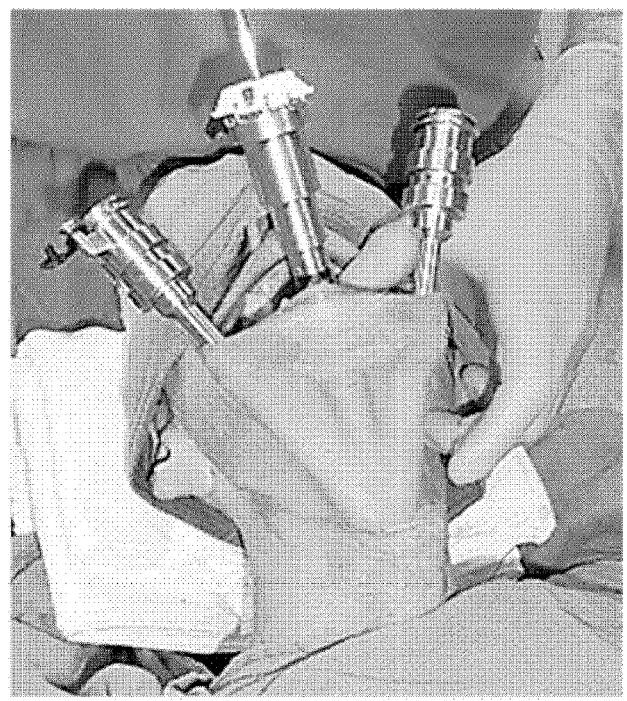
FIG. 13 shows a surgical retractor device used for thyroid retraction.

To compute the interaction applying in the direction of the deformation of the buckling beams, a controller may first derive the force analysis for the beam and obtain the following force/moment equation (see FIG. 13 for notations):

$$-EI \cdot \frac{d\psi}{ds} = F_x \cdot v(s) - F_v \cdot x(s) \quad (2)$$

where $v(s)=\int_0^s \sin\psi\, ds$, $x(s)=\int_0^s \cos\psi ds$. Also, the boundary conditions (B.C.) are $$\psi(1)=0, v(1)=\int_0^1 \sin\psi ds=0 \quad (3)$$

$$x(1)=\int_0^1 \cos\psi ds=1-a \quad (4)$$

Figure 15:
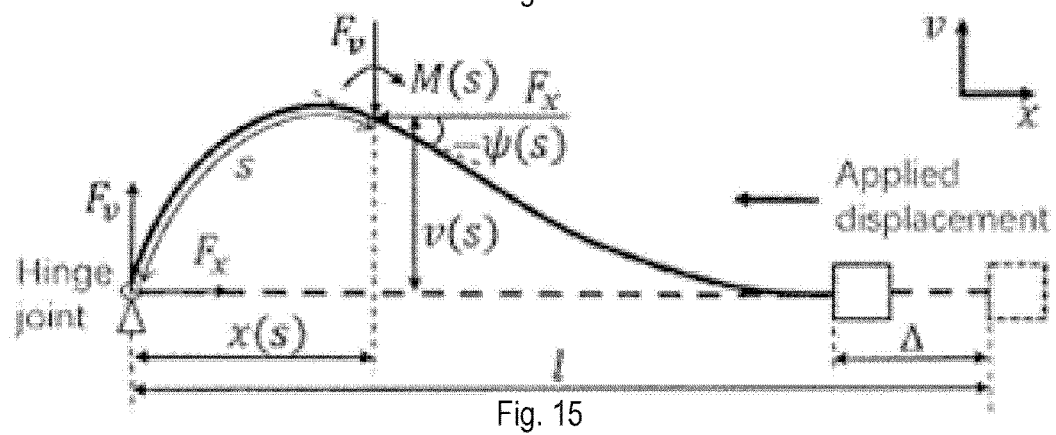
FIG. 15 shows a schematic force and bowing diagram of a retractor strut.

From here, the controller may address the force estimation problem for the struts using numerical iterative approach such as Extended Kalman Filter (EKF) with the model (Eq. 2). From FIG. 15, the inputs of the system are the pushing force $F_x$ and input displacement $x(s)$, which can be estimated by the controller through the motor current and encoder indirectly. With the identified force contact and measured shape, slope, and curvature of the beam along the segment using the fiber optic sensor, the inverse problem of the model in Eq. 2 is solved numerically by the controller.

Figure 6A:
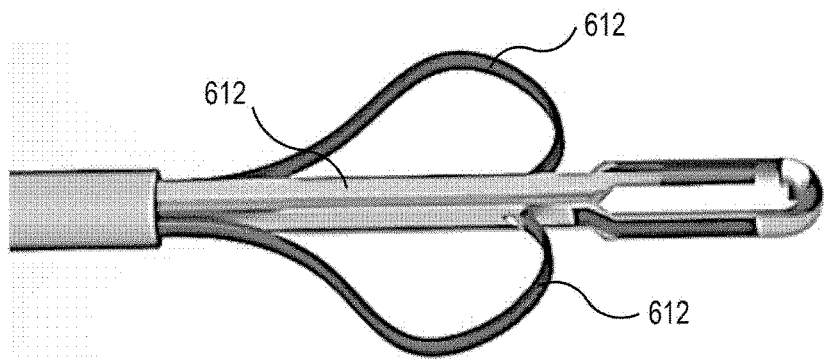
FIGS. 6A-6E show embodiments of surgical retractor devices with two pairs of retractor struts.
Figure 6B:
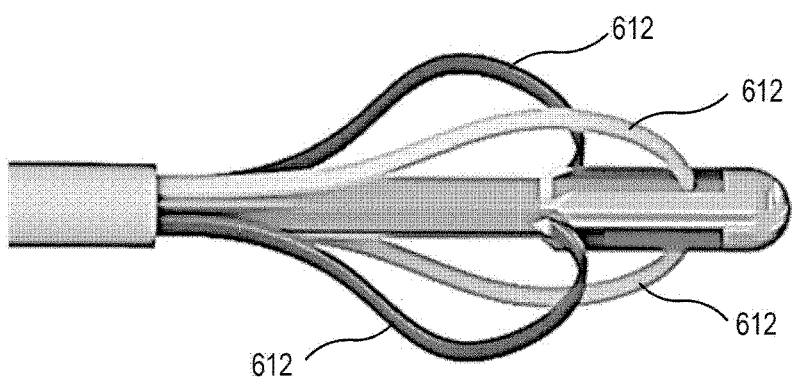
Figure 6C:
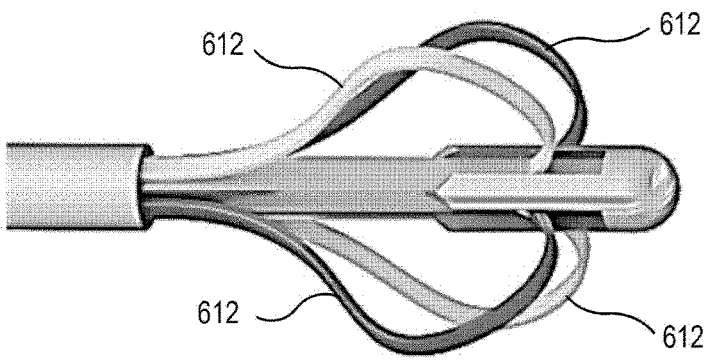

In embodiments, the first shaft may include a plurality of pairs of retractor struts, for example 2, 3 or 4 pairs, similar or identical to the retractor struts disclosed above. For example, as shown in FIG. 6A a device may include two pairs of retractor struts 612. In embodiments, when in the expanded configuration the retractor struts 612 are in orthogonal planes, for example as shown in FIG. 6B. In embodiments, for example as shown in FIG. 6C, distal ends of the retractor struts 612 may be coupled to the first shaft at different distal positions.

Figure 6D:
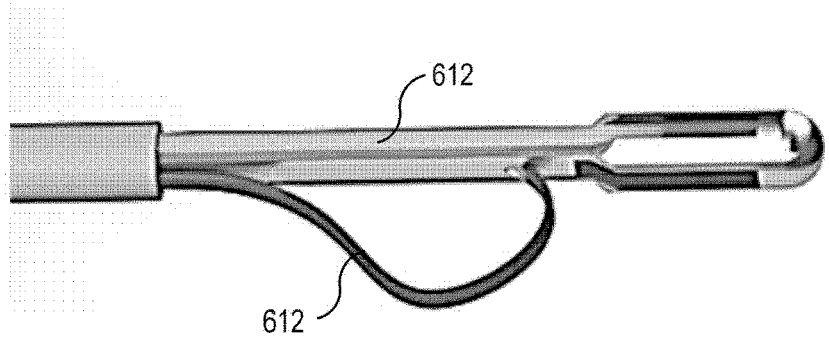
Figure 6E:
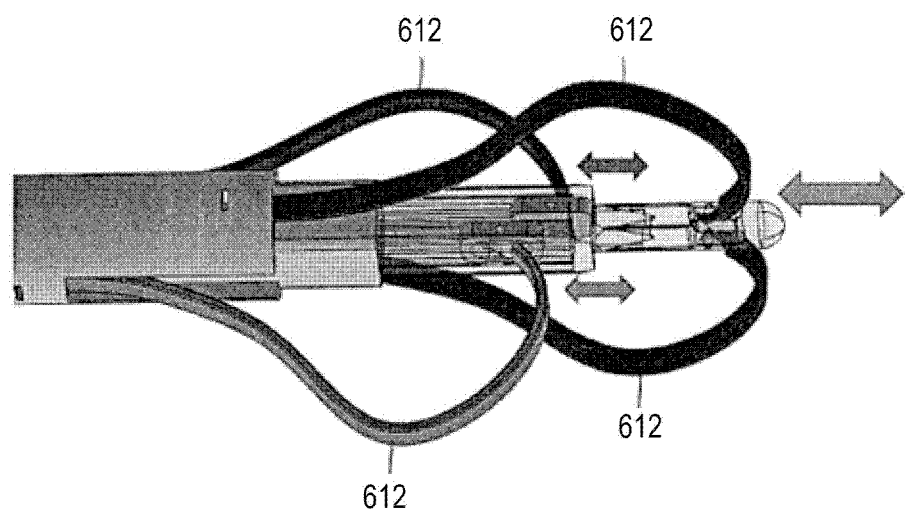

The plurality of pairs of retractor struts may be mechanically coupled in order to be synchronously actuated between the collapsed state and expanded state. In embodiments, each of the pairs of retractor struts, or an individual retractor strut, may be actuated independently. In embodiments, retractor struts may not be in pairs. Further, in embodiments, single retractor struts may be actuated independently of other retractor struts, for example as shown in FIGS. 6D and 6E. Retractor struts of a device may have the same or different lengths, the same or different bowing properties, and/or may be actuated to have different degrees of bowing in order to retract organs to different extents around the longitudinal axis of the first shaft.

Articulating Joints

A surgical retractor device may include a plurality of shafts linked together between the distal end and a proximal end, wherein during use the proximal end is external to the patient. One or more of the shaft may be linked with articulating joints. The articulating joints may be controlled automatically and/or manually.

Figure 7A:
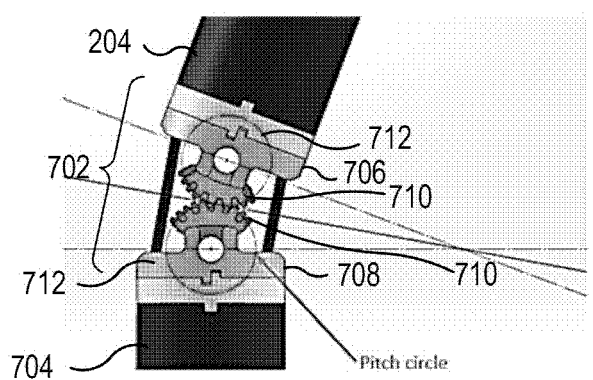
FIGS. 7A-7D show an articulating joint.
Figure 7B:
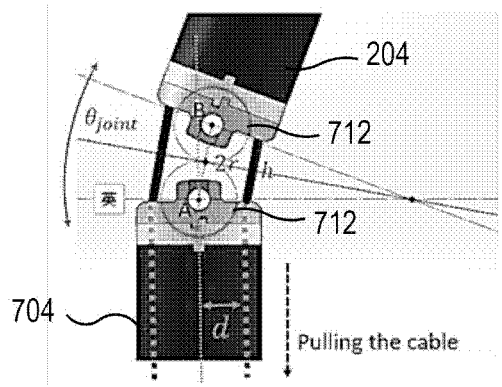
Figure 7C:
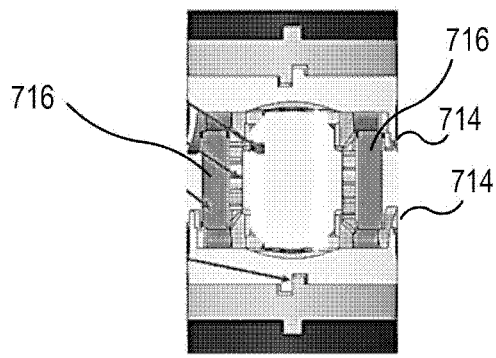
Figure 7D:
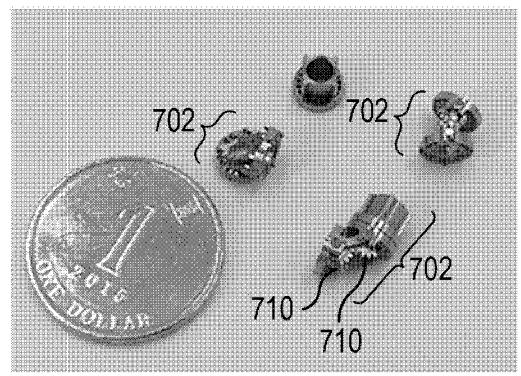

As shown in FIG. 7A, the first shaft 204 may be coupled to a third shaft 704 with an articulating joint 702. The articulating joint 702 comprises a first joint portion 706 coupled to the first shaft 204 and a second joint portion 708 coupled to the third shaft 704. Each of the first and second joint portions comprises a pair of rolling gears 710. The pair of rolling gears may be positioned on opposite sides of the longitudinal axis of the shaft so that cabling, optical fibers, working lumens, and/or wiring extending through lumens in the shafts may extend between adjacent shafts. The rolling gears 710 include gear teeth extending around a portion around a pitch circle 712 of the rolling gears. The rolling gears 710 are meshed and the degrees that the gear teeth extend around the pitch circle define a range of motion of the articulating joint. For example, the gear teeth may extend 90 degrees around the pitch circle defining 90 degrees of range of motion between a longitudinal axes of the first and third shafts. In embodiments, the range of motion defined by the gear teeth around the pitch circle may be greater or less than 90 degrees and may be determined based on the intended navigation needs of placing the retractor device at the desired surgical site.

The first and second joint portions may further include abutment faces 714 which define a mechanical hard stops for limiting the range of motion defined by the meshed rolling gears. The meshed rolling gears provide the advantage of preventing slippage of the articulating joint which allows for increased payloads compared to non-gear joints, for example a rolling joint mechanism.

Figure 10A:
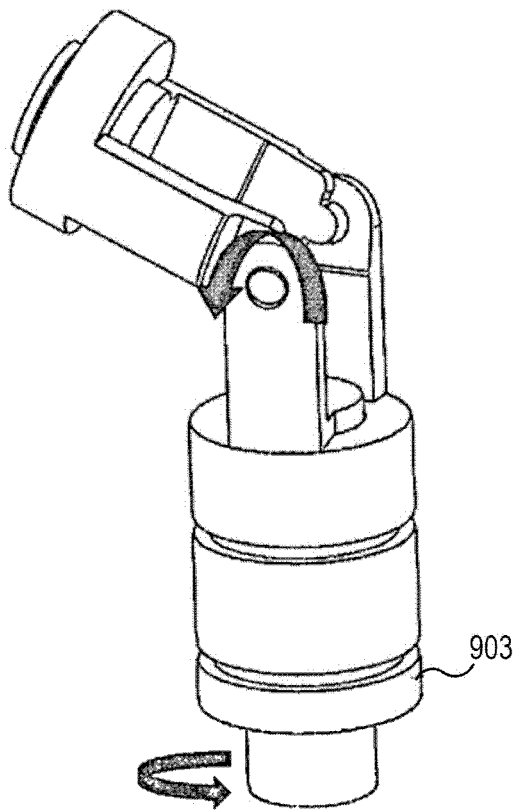
FIGS. 10A-10B show an embodiment of an articulating joint.
Figure 10B:
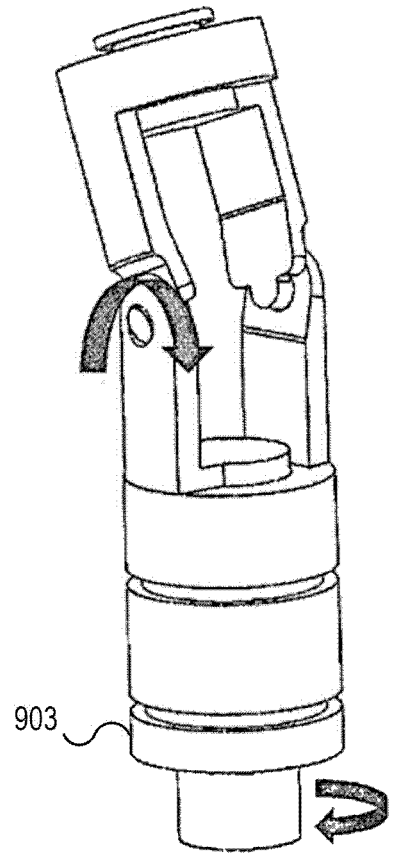
Figure 10C:
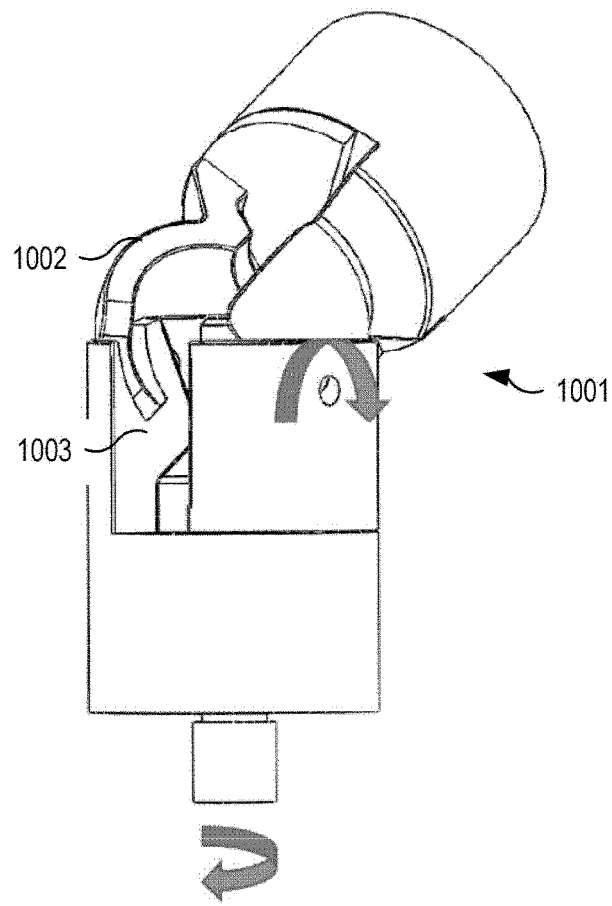
FIGS. 10C-10D show an embodiment of an articulating joint.
Figure 10D:
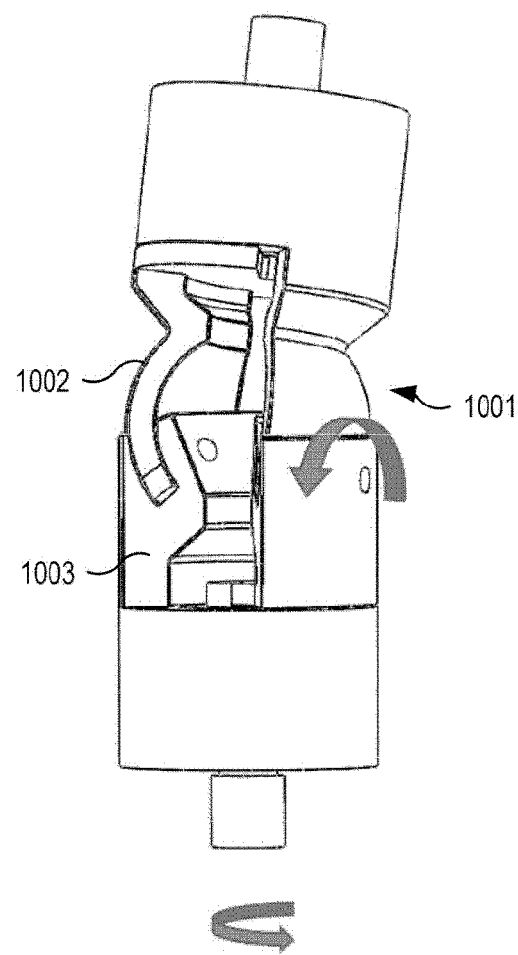

In embodiments, in order to prevent relative translation of the first and third shafts and limit the movement to relative angular motion between the first shaft and the third shaft the articulating joint further includes a linkage 716 rotationally coupled to the first rolling gear 710 at a center of the pitch circle 712, and rotationally coupled to the second rolling gear 710 at a center of the pitch circle 712. As shown, the linkage may define a dumbbell shape. The linkage prevents the gears from being pressed into each other causing increased friction and prevents the gears from being pulled apart and unmeshed. The meshing of the rolling gears and the linkage define a pure rolling motion, without any transverse and axial split of the contact which ensures high torsional stiffness. In embodiments, an articulating joint may include a spherical four bar linkage joint, including a meshing spherical gears 901 between the rolling gears 710, as shown for example in FIGS. 9A and 9B. Further, as shown in FIGS. 9A, 9B, 10A and 10B, in embodiments articulation may also comprise a distal roll component 903 allowing the distal end to be able to rotate up to 360 degree to provide extra dexterity. Further in embodiments, for example as shown in FIGS. 10C and 10D, articulation may comprise a ball and socket joint 1001, comprising a ball 1002 and a socket 1003. The ball and socket joint allows for articulation in three rotational degrees of freedom. Further, embodiments including ball and socket joints may further include distal roll components 903.

Figure 8:
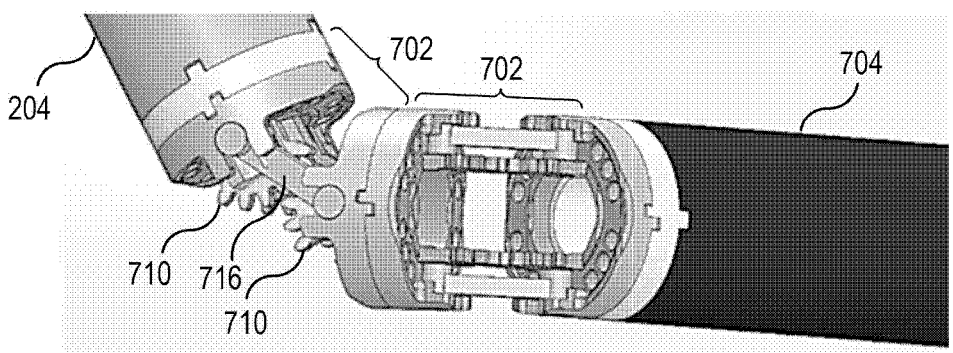
FIG. 8 shows a pair of sequentially coupled articulating joints.
Figure 9A:
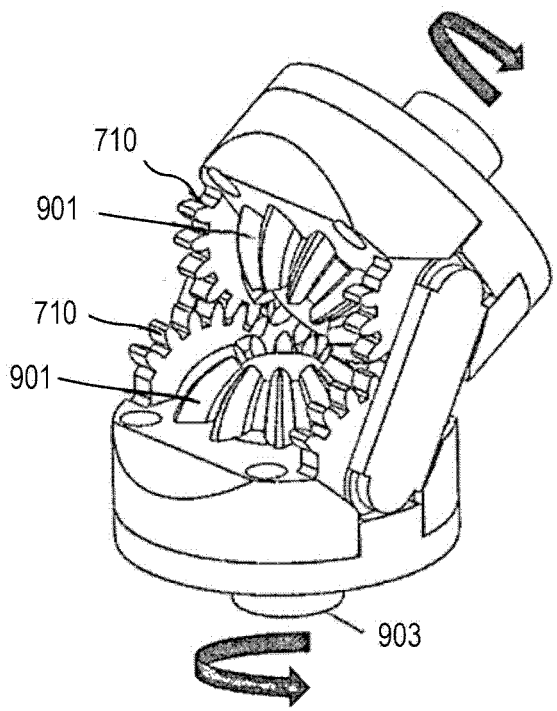
FIGS. 9A-9B show an embodiment of an articulating roll joint.
Figure 9B:
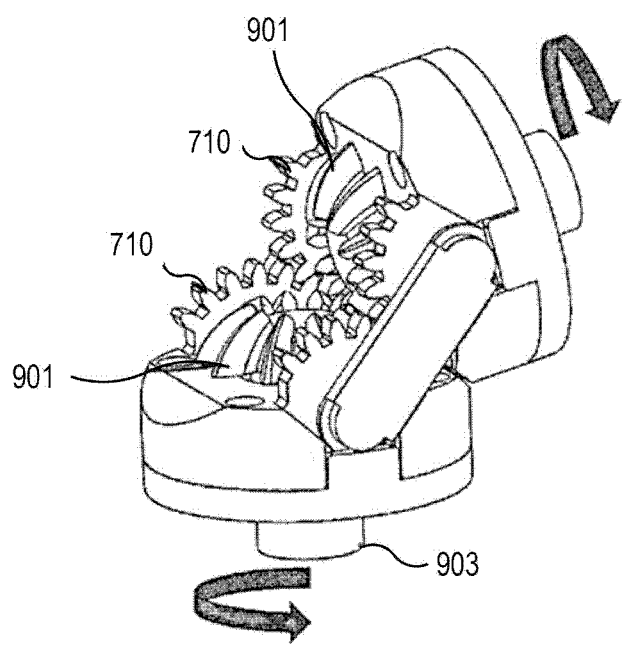

In embodiments, two articulating joints 702 may be sequentially coupled together between two shafts, as shown in FIG. 8. The two articulating joints may be oriented orthogonally relative to each other so that the planes that the joints rotate through are orthogonal in order to define two independent degrees of freedom, e.g. pitch and yaw relative to a horizontal reference frame shaft. In embodiments, the two articulating joints may be oriented non-orthogonal arrangements in order to increase ranges of motions in select degrees of freedom.

In embodiments, the articulating joints may be coupled to an actuation mechanism. Actuation of the articulation joints may be cable driven, linkage driven, pneumatically driver, hydraulically, driver, and/or magnetically driver. In embodiments, the articulating joints are driven with a pair of cables, for example Bowden cables, that extend through the shafts from the articulating joint to an external actuation device. The cables may be attached to opposite sides of the rolling gear on the distal joint portion. Shortening one cable and lengthening the other will cause the joint to rotate in the direction of the shortened cable. The cables of any distally located articulating joints, as well as the cables of distally located retractor struts, may extend through the central lumens of proximally located articulating joints, and proximally located shafts, and terminate at the external actuation device.

The length of the cables may be adjusted manually directly by a user and/or automatically by a controller. For example, the device may include a handle with manual user controls, for example levers, buttons, knobs, or pull tabs, that allow a user to directly manipulate the lengths of the cables, and in turn allow for manipulation of the articulating joints. In embodiments, the external body may include one or more powered actuators, for example motor pulleys or linear actuators, coupled to the cables and coupled to a controller for automatically actuating the articulating joints. In embodiments, actuators, for example micro-motors, may be included in the shafts of the device. The actuators may be compatible with a robotic surgical platform such as the "daVinci Research Kit (dVRK)", see Kazanzides P, Chen Z, Deguet A, Fischer G S, Taylor R H, DiMaio S P, "An Open-Source Research Kit for the da Vinci Surgical System", International Conference on Robotics and Automation, ICRA 2014, May 2014 which is incorporated by reference in its entirety. In embodiments, the external actuator body may be mounted to a stationary structure or a robotic arm. In embodiments, the external actuator body may be a handle and includes controls for a user to mechanically, or electrically, actuate the retractor struts and/or the articulating joints.

Figure 11:
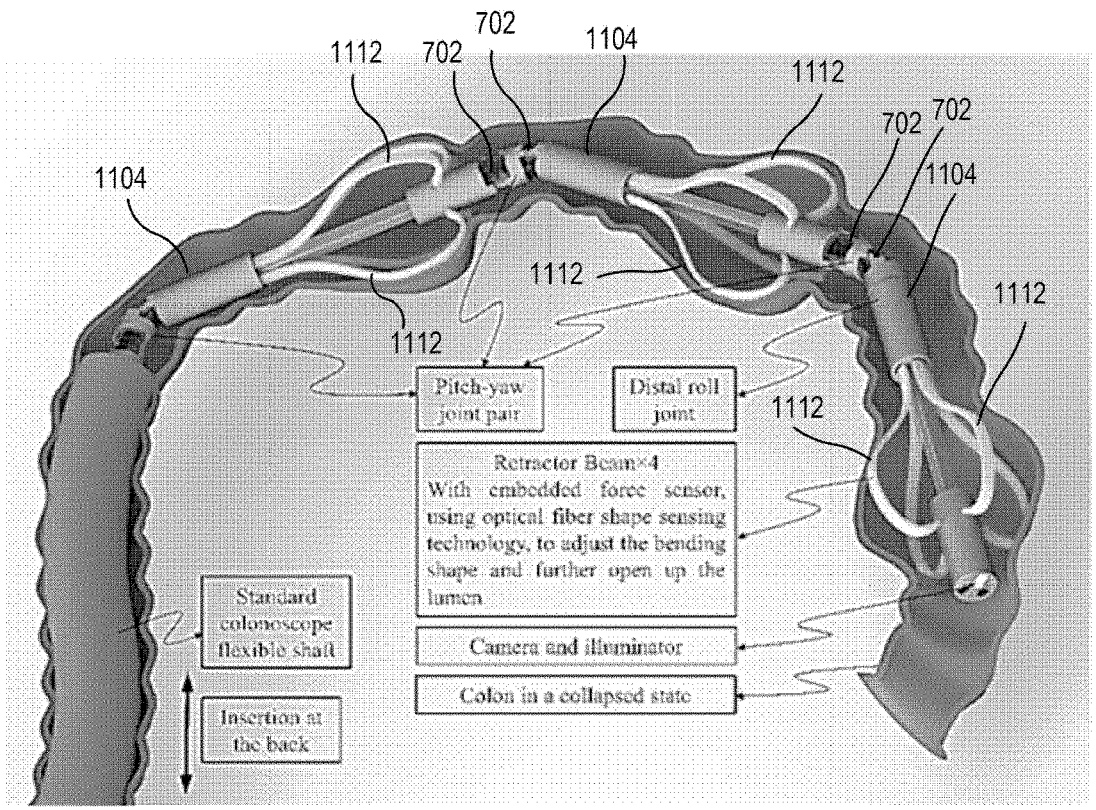
FIG. 11 shows an embodiment of a surgical retractor device multiple shafts each with a pair of retractor struts.

In embodiments, a device may include multiple shafts each with one or more pairs of retractor struts, as disclosed above. One or more of the couplings between adjacent shafts may comprise one or more articulating joints to achieve one or more degrees of freedom between adjacent shafts. Advantages of such embodiments include coordinated control, directly by a user and/or a controller, of the multiple compliant retractor tips and articulated joints to allow for irregular shape opening and organ retraction. An example of a multi shaft device is shown in FIG. 11. As shown, the device includes three shafts 1104 each with two pairs of retractor struts 1112. Further as shown, the coupling between adjacent shafts includes two articulating joints 702 as disclosed above in order to achieve two degrees of freedom, e.g. pitch and yaw. Further, in embodiments, devices may comprise a roll joint, for example as part of an articulating joint, for example as shown in FIGS. 10A and 10B, in order to achieve a third degree of freedom, i.e. roll. Three rotational degrees of freedom allow for precise placement and orientation of the retractor struts in the bowed configuration. Further, an articulated retractor with a distal roll allows for opening up space with highly collapsed organs, for example the colon, and further allows application of a direct torque at the distal end of the instrument.

As noted, actuators for actuating the one or more retractor struts and/or the one or more articulating joints; as well as the one or more sensors may be coupled to a controller. In embodiments, the controller is further coupled to additional surgical devices, for example graspers, needle drivers, forceps, scissors, small clip applier, and bipolar cautery, as well as one or more additional sensors, for example one or more cameras. For example, a retractor device may be coupled to a da Vinci Research Kit.

Visual Feedback System

Figure 12:
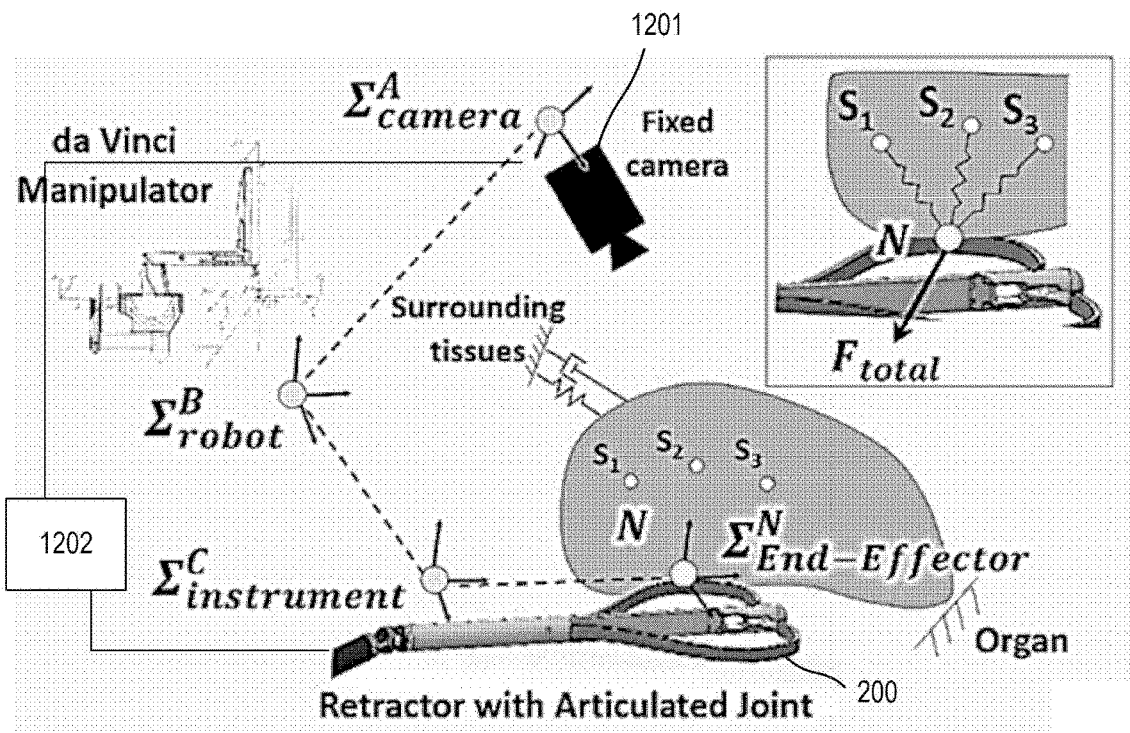
FIG. 12 shows an embodiment of a system with a surgical retractor device and a camera.

FIG. 12 shows an embodiment of a system including a retractor device 200, for example as disclosed above, and a camera 1201. Visualization of the retractor device by the camera may be used for semi-autonomous or autonomous retraction and space opening. The camera feedback, alone or in addition to force sensor feedback, as discussed above, may be used by the controller 1202 to determine organ deformation and retraction. Using the camera and force sensors in this manner allows for the load of the organ to be evenly distributed onto the organ, preventing overly stressing the organ tissue, while still maximize the space for surgical intervention.

In embodiments, feedback from the camera may be used by the controller to detect the organ that is being retracted, the amount that the organ is being retracted, the amount or shape of bowing of one or more of the retractor struts, the positions of one or more points of the retractor device, and/or the positions of one or more points on other surgical devices. The feedback may be used to provide coordinated control of multiple compliant tip retractor devices to allow irregular shape opening and organ retraction. Information determined with a camera may be used in combination with information from the sensors integrated into the retraction device in order to automatically and continually adjust the position of the components of the retractor device.

In embodiments, feedback from the sensors integrated into the retractor device, and/or other sensors, may be used by the controller to initiate a transition from the collapsed state to the expanded state, including determining the degree of bowing to achieve a desired retraction amount. Further, during retraction, the feedback may be used to adjust one or more retractor struts and/or one or more articulating joints in order to maintain a desired retraction amount of an organ, to maintain a force applied by the retractor device to a level below a predetermined threshold associated with damage to the organ, and/or to continuously adjust the shape of the retractor struts to a desired shape.

Methods of Use

Figure 3:
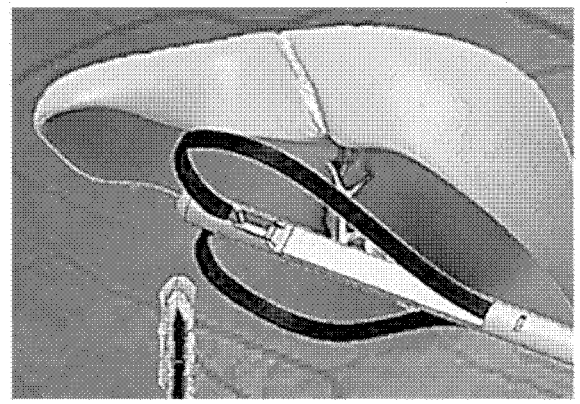
FIG. 3 shows a surgical retractor device retracting an organ.
Figure 14:
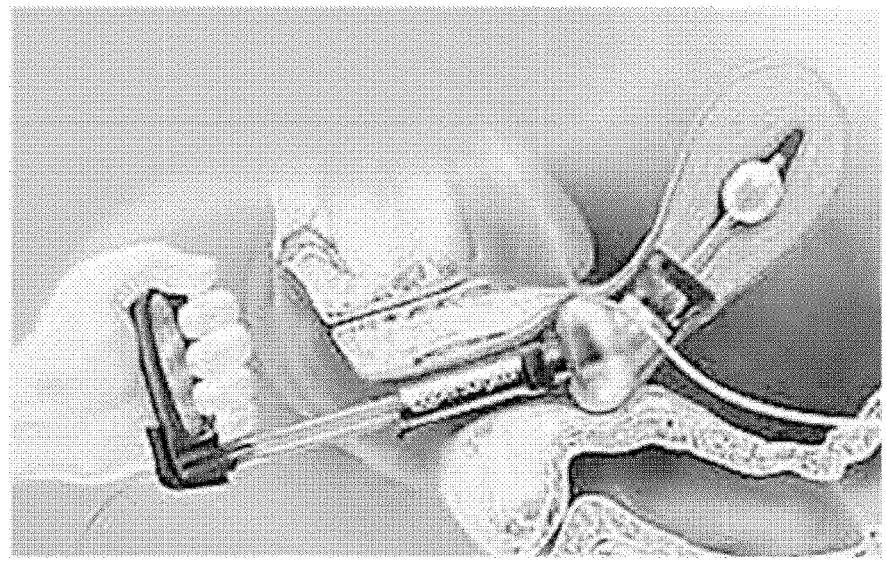
FIG. 14 shows a surgical retractor device used for uterus manipulation.

The present technology may be used in a variety of surgical applications, including minimally invasive surgeries. The present technology may be used as a retractor and/or a space opener in different clinical applications such as transoral thyroid retraction (FIG. 13), liver retraction (FIG. 3), colon retraction (FIG. 11) and retractor for uterus manipulation (FIG. 14).

For example, as shown in FIG. 11, a retractor device as shown in FIG. 2A, is placed through an incision into a surgical space near the thyroid of the patient in the collapsed configuration. Placement of the retractor device may be fully automated using a surgical navigation system, which may include a camera as disclosed above. The orientation of the retractor struts may be adjusted by the controller so the direction of bowing of the one or more individual or pairs of retractor struts will cause an in organ, in this example the thyroid, to be retracted. When in the correct orientation, the first shaft is actuated by the controller to cause the retractor struts to bow and press against the organ, in this example thyroid. In embodiments, feedback from the integrated optical fiber sensors may be used by the controller during the transition between the collapsed state and the expanded state in order for the controller to determine if an appropriate retraction force or stress is reached, which is below a retraction force or stress known to cause tissue damage, which may be pre-stored in the controller and/or input by an operator Once in an expanded configuration, the retraction force or stress may be automatically monitored by the controller and the amount of bowing of the retractor struts may be continuously adjusted by the controller, and/or the position of the distal end may be adjusted via an articulating joint in order to maintain an appropriate pressing force or stress. In embodiments, if a threshold force or stress associated with organ damage is detected automatic collapse of the retractor struts from the bowed configuration may be performed by the controller. Once the surgery is complete, the retractor struts may be transitioned back to the collapsed state by the controller and then the distal end may be manually or automatically navigated out of the surgical space. Similar or the same steps may be performed at other organ retraction or space opening locations. For example, a device may be inserted into an incision through the abdomen of a patient in the collapsed configuration, then expanded to retract a liver of a patient, and then continually and automatically monitored and adjusted as discussed above. Further, devices may be used in existing body orifices. For example, a device with multiple shafts each with retractor struts may be inserted into the colon of a patient with each retractor strut in a collapsed configuration. The retractor devices of each shaft may be individually monitored and adjusted by the controller. The articulating joints connecting the shafts may be used to conform the device to the shape of the colon as the distal end is navigated to a desired location. Once positioned in a desired location with a desired shape, the retractor struts are transitioned to the expanded configuration by the controller. The force and amount of retraction of each retractor strut may be continually and automatically monitored and adjusted as discussed above. Once surgery is complete, each retractor strut may be collapsed and the device may be automatically navigated out of the colon with the use of the articulating joints between the shafts. In embodiments, devices may further be used in the uterus, similarly as in the colon. For example, a collapsed device may be inserted through the cervix into the uterus and then expanded for retraction of the uterus.

The various aspects, embodiments, implementations or features of the described embodiments can be used separately or in any combination. In particular, it should be appreciated that the various elements of concepts from FIGS. 1-15 may be combined without departing from the spirit or scope of the invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, or gradients thereof, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. The invention is susceptible to various modifications and alternative constructions, and certain shown exemplary embodiments thereof are shown in the drawings and have been described above in detail. Variations of those preferred embodiments, within the spirit of the present invention, may become apparent to those of ordinary skill in the art upon reading the foregoing description. The inventors expect skilled artisans to employ such variations as appropriate, and the inventors intend for the invention to be practiced otherwise than as specifically described herein. Accordingly, it should be understood that there is no intention to limit the invention to the specific form or forms disclosed, but on the contrary, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A system for organ retraction comprising:
a surgical retraction device, comprising:
a first shaft comprising a distal end and a proximal end extending along a longitudinal axis;
a first pair of retractor struts extending from the distal end toward the proximal end, wherein the first pair of retractor struts are configured to be positionable between a collapsed configuration with the first pair of retractor struts substantially parallel to the longitudinal axis, and an expanded configuration with middle portions of the first pair of retractor struts bowed away from the longitudinal axis in opposite directions within a same plane, wherein in the expanded configuration the first pair of retractor struts are configured to retract an organ of a patient during a surgical procedure; and
a second shaft extending along the longitudinal axis,
wherein the second shaft is configured to translate relative to the first shaft along the longitudinal axis,
wherein the second shaft is positioned to translate within the first shaft,
wherein a distal portion of each of the first pair of retractor struts is affixed proximal to the distal end of the first shaft and a proximal portion of each of the first pair of retractor struts is affixed to the second shaft,
wherein translating the second shaft toward the distal end of the first shaft causes the first pair of retractor struts to transition between the collapsed configuration and the expanded configuration,
wherein a degree of bowing of the first pair of retractor struts is based on a relative position of the first shaft and the second shaft; and
a controller configured to actuate the first pair of retractor struts between the collapsed configuration and the expanded configuration, determine an amount of bowing of the first pair of retractor struts or an amount of organ retraction performed by the first pair of retractor struts, and based on the determined amount adjust bowing the first pair of retractor struts during the surgical procedure, wherein the controller is configured to translate the second shaft relative to the first shaft.

2. The system of claim 1, wherein the controller is configured to continually select the degree of bowing or a shape of the first pair of retractor struts based on a desired amount of organ retraction.

3. The system of claim 1, wherein each of the first pair of retractor struts comprises a metal beam, a plastic beam, or a composite beam, and
wherein the controller is configured to determine the amount of bowing of the first pair of retractor struts or the amount of organ retraction performed by the first pair of retractor struts based on material properties of materials which comprise the first pair of retractor struts.

4. The system of claim 3, wherein each of the first pair of retractor struts comprises a metal beam and wherein the metal beam is a shape metal alloy.

5. The system of claim 1, further comprising a user interface body, wherein the user interface body comprises an actuation mechanism connected to the controller and configured to translate the second shaft relative to the first shaft.

6. A method for organ retraction comprising:
inserting the surgical retraction device of claim 1, with the controller, into a surgical space of a patient in the collapsed configuration; and
positioning the first pair of retractor struts proximate to an organ and transitioning the first pair of retractor struts to the expanded configuration, with the controller, in order to retract the organ.

7. The method of claim 6, wherein the first pair of retractor struts comprise one or more force sensors connected to the controller, and
wherein the method further comprises determining with the one or more force sensors a retractor strut property comprising an amount of organ retraction, an amount of retraction force, and/or an amount of bowing of the first pair of retractor struts.

8. The method of claim 7, further comprising:
adjusting an amount of retraction force applied by the first pair of the retractor struts in order to minimize the retraction force by continuously adjusting a position of the first pair of retractor struts while maintaining a desired visualization of a target site.

9. A system for organ retraction comprising:
a surgical retraction device, comprising:
a first shaft comprising a distal end and a proximal end extending along a longitudinal axis;
a first pair of retractor struts extending from the distal end toward the proximal end, wherein the first pair of retractor struts are configured to be positionable between a collapsed configuration with the first pair of retractor struts substantially parallel to the longitudinal axis, and an expanded configuration with middle portions of the first pair of retractor struts bowed away from the longitudinal axis in opposite directions within a same plane, wherein in the expanded configuration the first pair of retractor struts are configured to retract an organ of a patient during a surgical procedure,
wherein each of the first pair of retractor struts comprises a metal beam, a plastic beam, or a composite beam,
wherein the metal beam is coated with a coating material configured to have greater friction against an organ than the metal beam in order to provide hold friction for the organ retraction in order to reduce sliding between the organ and the first pair of retractor struts, and
a controller configured to actuate the first pair of retractor struts between the collapsed configuration and the expanded configuration, determine an amount of bowing of the first pair of retractor struts or an amount of organ retraction performed by the first pair of retractor struts, and based on the determined amount adjust bowing the first pair of retractor struts during the surgical procedure,
wherein the controller is configured to determine the amount of bowing of the first pair of retractor struts or the amount of organ retraction performed by the first pair of retractor struts based on material properties of materials which comprise the first pair of retractor struts,
wherein the controller is configured to determine the amount of organ retraction performed by the first pair of retractor struts based on the friction between the coating material and the organ.

10. A system for organ retraction comprising:
a surgical retraction device, comprising:
a first shaft comprising a distal end and a proximal end extending along a longitudinal axis;
a first pair of retractor struts extending from the distal end toward the proximal end, wherein the first pair of retractor struts are configured to be positionable between a collapsed configuration with the first pair of retractor struts substantially parallel to the longitudinal axis, and an expanded configuration with middle portions of the first pair of retractor struts bowed away from the longitudinal axis in opposite directions within a same plane, wherein in the expanded configuration the first pair of retractor struts are configured to retract an organ of a patient during a surgical procedure; and a second pair of retractor struts extending from the distal end toward the proximal end, wherein the second pair of retractor struts are configured to be positionable between the collapsed configuration with the second pair of retractor struts substantially parallel to the longitudinal axis, and the expanded configuration with middle portions of the second pair of retractor struts bowed away from the longitudinal axis, wherein in the expanded configuration the first pair of retractor struts are bowed in a first plane, and the second pair of retractor struts are bowed in a second plane orthogonal to the first plane; and a controller configured to actuate the first pair of retractor struts between the collapsed configuration and the expanded configuration, determine an amount of bowing of the first pair of retractor struts or an amount of organ retraction performed by the first pair of retractor struts, and based on the determined amount adjust bowing the first pair of retractor struts during the surgical procedure, wherein the controller is configured to individually actuate the first pair of retractor struts and the second pair of retractor struts.

11. A system for organ retraction comprising:
a surgical retraction device, comprising:
a first shaft comprising a distal end and a proximal end extending along a longitudinal axis;
a first pair of retractor struts extending from the distal end toward the proximal end, wherein the first pair of retractor struts are configured to be positionable between a collapsed configuration with the first pair of retractor struts substantially parallel to the longitudinal axis, and an expanded configuration with middle portions of the first pair of retractor struts bowed away from the longitudinal axis in opposite directions within a same plane, wherein in the expanded configuration the first pair of retractor struts are configured to retract an organ of a patient during a surgical procedure; and
a third shaft coupled to the first shaft with an articulated joint, wherein the third shaft extends along a second longitudinal axis,
wherein the articulated jointed comprises:
a first rolling gear coupled to the first shaft relative to the longitudinal axis, and
a second rolling gear coupled to the third shaft relative to the second longitudinal axis,
wherein the first rolling gear meshes with the second rolling gear in order to allow relative angular motion between the first shaft and the third shaft in order to change an angle between the longitudinal axis and the second longitudinal axis; and
a controller configured to actuate the first pair of retractor struts between the collapsed configuration and the expanded configuration, determine an amount of bowing of the first pair of retractor struts or an amount of organ retraction performed by the first pair of retractor struts, and based on the determined amount adjust bowing the first pair of retractor struts during the surgical procedure.

12. A surgical retraction device, comprising:
a first shaft comprising a distal end and a proximal end extending along a longitudinal axis;
a first pair of retractor struts extending from the distal end toward the proximal end, wherein the first pair of retractor struts are configured to be positionable between a collapsed configuration with the first pair of retractor struts substantially parallel to the longitudinal axis, and an expanded configuration with middle portions of the first pair of retractor struts bowed away from the longitudinal axis in opposite directions within a same plane, wherein in the expanded configuration the first pair of retractor struts are configured to retract an organ of a patient during a surgical procedure, and
a third shaft coupled to the first shaft with an articulated joint, wherein the third shaft extends along a second longitudinal axis,
wherein the articulated jointed comprises:
a first rolling gear coupled to the first shaft relative to the longitudinal axis, and
a second rolling gear coupled to the third shaft relative to the second longitudinal axis, and
wherein the first rolling gear meshes with the second rolling gear in order to allow relative angular motion between the first shaft and the third shaft in order to change an angle between the longitudinal axis and the second longitudinal axis.

13. A system for organ retraction comprising:
a surgical retraction device, comprising:
a first shaft comprising a distal end and a proximal end extending along a longitudinal axis;
a first pair of retractor struts extending from the distal end toward the proximal end, wherein the first pair of retractor struts are configured to be positionable between a collapsed configuration with the first pair of retractor struts substantially parallel to the longitudinal axis, and an expanded configuration with middle portions of the first pair of retractor struts bowed away from the longitudinal axis in opposite directions within a same plane, wherein in the expanded configuration the first pair of retractor struts are configured to retract an organ of a patient during a surgical procedure; and
a controller configured to actuate the first pair of retractor struts between the collapsed configuration and the expanded configuration, determine an amount of bowing of the first pair of retractor struts or an amount of organ retraction performed by the first pair of retractor struts, and based on the determined amount adjust bowing the first pair of retractor struts during the surgical procedure,
wherein the first pair of retractor struts comprise one or more force sensors connected to the controller and configured to sense external forces on the retractor struts.

14. The system of claim 13, wherein the force sensor comprises an optical fiber extending around one of the first pair of retractor struts in a tortuous path.

15. The system of claim 1, wherein the second shaft comprise one or more force sensors configured to sense deflection of the first pair of retractor struts.

16. The system of claim 13, further comprising:
a camera
wherein the controller is further configured to determine the amount of organ retraction with feedback from the force sensors and the camera, and
based on the determined amount of organ retraction adjust bowing the first pair of retractor struts.

17. A surgical retraction device, comprising:
a first shaft comprising a distal end and a proximal end extending along a longitudinal axis;
a first pair of retractor struts extending from the distal end toward the proximal end, wherein the first pair of retractor struts are configured to be positionable between a collapsed configuration with the first pair of retractor struts substantially parallel to the longitudinal axis, and an expanded configuration with middle portions of the first pair of retractor struts bowed away from the longitudinal axis in opposite directions within a same plane,
wherein in the expanded configuration the first pair of retractor struts are configured to retract an organ of a patient during a surgical procedure,
wherein the first pair of retractor struts comprise a material configured to transition between a first state and a second state based on temperature,
wherein the material is a shape metal alloy, and
wherein transitioning the material from the first state to the second state causes the retractor struts to transition from the collapsed configuration to the expanded configuration.

18. The surgical retraction device of claim 17, wherein the first state is a martensite state and the second state is an austenite state.

19. The surgical retraction device of claim 17, further comprising a heater configured to heat the material to cause a transition from the first state to the second state.

\* \* \* \* \*